United States Patent
Takechi et al.

Patent Number: 6,022,564
Date of Patent: Feb. 8, 2000

[54] METHOD FOR PRODUCING A MICROPARTICLE

[75] Inventors: Nobuyuki Takechi, Osaka; Muneo Nonomura, Toyonaka; Shigehiro Higuchi, Amagasaki; Toshiharu Beppu, Nishinomiya, all of Japan

[73] Assignee: Takeda Chemical Industries, Ltd., Osaka, Japan

[21] Appl. No.: 09/260,797

[22] Filed: Mar. 1, 1999

Related U.S. Application Data

[63] Continuation of application No. PCT/JP97/03608, Oct. 8, 1997.

[30] Foreign Application Priority Data

Oct. 9, 1996 [JP] Japan .................................. 8-268704

[51] Int. Cl.⁷ .................................................. B02C 23/06
[52] U.S. Cl. ...................... 424/489; 424/501; 514/211; 514/224.2
[58] Field of Search .................. 424/489, 501; 514/211, 224.2

[56] References Cited

U.S. PATENT DOCUMENTS

| | | |
|---|---|---|
| 5,134,122 | 7/1992 | Orsolini . |
| 5,213,812 | 5/1993 | Ruiz ........................................ 424/495 |
| 5,225,205 | 7/1993 | Orsolini . |
| 5,439,688 | 8/1995 | Ovsolini et al. . |
| 5,567,431 | 10/1996 | Vert ........................................ 424/426 |

FOREIGN PATENT DOCUMENTS

| | | |
|---|---|---|
| 0376197 A1 | 7/1990 | European Pat. Off. . |
| 0460488 A1 | 12/1991 | European Pat. Off. . |
| 0535937 A1 | 4/1993 | European Pat. Off. . |
| 0719782 A1 | 7/1996 | European Pat. Off. . |
| 2234169 | 1/1991 | United Kingdom . |

*Primary Examiner*—Nathan M. Nutter
*Attorney, Agent, or Firm*—Philippe Y. Riesen

[57] ABSTRACT

This invention provides a method for producing a microparticle which comprises pulverizing a solid preparation comprising a compound represented by the formula:

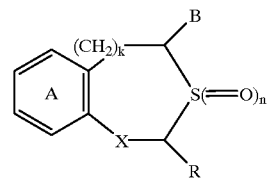

wherein ring A is an optionally substituted benzene ring; R is a hydrogen atom or an optionally substituted hydrocarbon group; B is an optionally esterified or amidated carboxyl group; X is —CH(OH)— or —CO—; k is 0 or 1; and n is 0, 1 or 2 or a pharmaceutically acceptable salt thereof and a biodegradable polymer of α-hydroxycarboxylic acid in the presence of a pulverizing auxiliary, which can provide microparticles which are less adhesive and involve less aggregation and are thus excellent in drug entrapment ratio and control of drug-release in a desired particle size.

15 Claims, No Drawings

METHOD FOR PRODUCING A MICROPARTICLE

This application is a continuation of international application number PCTJP/97-03608, filed Oct. 8, 1997.

TECHNICAL FIELD

The present invention relates to a method for producing a microparticle. More specifically, the method of the present invention provides a microparticle having good dispersion ability and which does not substantially adhere or aggregate together.

BACKGROUND ART

The prior art includes, as disclosed in EP-A-481,732, a sustained-release preparation comprising a drug, a polylactic acid and a glycolic acid-hydroxycarboxylic acid [HOCE ($C_{2-8}$ alkyl)COOH] copolymer. The disclosed process comprises preparing a water-in-oil (W/O) emulsion consisting of an internal water phase consisting of an aqueous solution of a physiologically active peptide and an external oil phase consisting of a solution of a biodegradable polymer in an organic solvent, adding said W/O emulsion to a medium such as water and processing the resulting W/O/W emulsion into sustained-release microcapsules (in-water drying method).

However, generally a microparticle prepared by the in-water drying method does not achieve a high drug content. In that method, the encapsulation rate of the microparticle varies widely among the lots and is easily influenced by expansion of the production scale.

A spray-drying method is also known in the art. Although the microparticles produced by this method usually have an adequate encapsulation rate, the quality of the particles varies widely according to the changes of production condition. Generally, a lot of the microparticles are aggregate or adhere together in this method. Also, the dispersion ability of the particles in an aqueous dispersion solvent is reduced as compared with that of in-water drying method.

Further, in the known method for preparing a microparticle by pulverizing a solid dispersion containing a drug and a biodegradable polymer, there is a problem that a solid dispersion prepared by using an adhesive drug, especially in a large amount, is unable to be pulverized by a general pulverizing technique.

DISCLOSURE OF INVENTION

The present inventors made extensive investigation to obtain sustained-release microparticles (e.g. microcapsules) which rarely aggregate or adhere to each other and have a good dispersion ability, and found that microparticles having an excellent quality, wherein aggregation or adhesion among the particles takes place in a small ratio, drug encapsulation rate is high and the initial release of the drug is controlled in a low rate in the releasing test, could be efficiently produced on a large scale in a method which comprises dissolving a drug and the polymer in a solvent which could dissolve them together to provide a solution, preparing a solid dispersion by drying the resultant solution under reduced pressure or in a manner analogous thereto and pulverizing the resultant solid dispersion in the presence of a pulverizing auxiliary.

Further, it was also found that the microparticles were imparted with a better dispersion ability by coating with a water-soluble polymer and/or a nonionic surfactant.

The present invention was accomplished as a result of further investigation made based on these findings.

Accordingly, the present invention relates to:

(1) a method for producing a microparticle which comprises pulverizing a solid preparation comprising a compound represented by the formula:

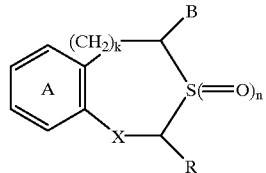

(I)

wherein ring A is an optionally substituted benzene ring; R is a hydrogen atom or an optionally substituted hydrocarbon group; B is an optionally esterified or amidated carboxyl group; X is —CH(OH)— or —CO—; k is 0 or 1; and n is 0, 1 or 2 or a pharmaceutically acceptable salt thereof and a biodegradable polymer of α-hydroxycarboxylic acid in the presence of a pulverizing auxiliary, (2) a method according to above (1), wherein the compound is a compound represented by the formula:

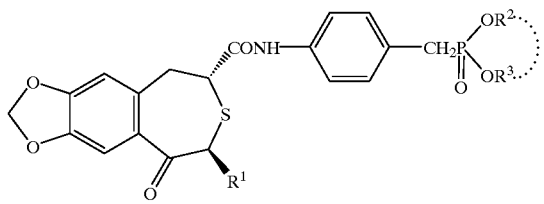

(II)

wherein $R^1$ is a hydrogen atom or an optionally substituted hydrocarbon group; and $R^2$ and $R^3$ are independently a lower alkyl group or bind together to form a lower alkylene group, (3) a method according to above (2), wherein $R^1$ is a methyl group, and $R^2$ and $R^3$ are ethyl group, (4) a method according to above (1), wherein the weight-average molecular weight of the polymer of the α-hydroxycarboxylic acid is about 3,000 to about 30,000, (5) a method according to above (1), wherein the α-hydroxycarboxylic acid is lactic acid and/or glycolic acid, (6) a method according to above (1), wherein the solid preparation is a solid dispersion, (7) a method according to above (1), wherein the pulverizing auxiliary is a sugar or a sugar alcohol, (8) a method according to above (1), wherein the pulverizing auxiliary is an organic acid, a salt thereof or a salt of an inorganic acid, (9) a method according to above (1), wherein the solid preparation is pulverized with a water-soluble polymer and/or a surfactant,

(10) a method according to above (1), which further comprises a step for coating the microparticle with a water-soluble polymer and/or a surfactant,

(11) a method according to above (9) or (10), wherein the surfactant is a nonionic surfactant,

(12) a method according to above (11), wherein the surfactant is pluronic F68,

(13) a method according to above (9) or (10), wherein the water-soluble polymer is a polyethylene glycol,

(14) a method according to above (13), wherein the polyethylene glycol is polyethylene glycol 4000,

(15) a method according to above (1), wherein the solid preparation is pulverized with an antiaggregation agent,

(16) a method according to above (1), which is followed by a step for dispersing the pulverized solid preparation to an aqueous dispersion solvent in the presence of an antiaggregation agent,

(17) a method according to above (15) or (16), wherein the antiaggregation agent is an amino acid,

(18) a method according to above (17), wherein the amino acid is arginine or cysteine,

(19) a method for producing a microparticle of (2R,4S)-(−)-N-[4-(diethoxyphosphorylmethyl)phenyl]-1,2,4,5-tetrahydro-4-methyl-7,8-methylenedioxy-5-oxo-3-benzothiepine-2-carboxamide or a pharmaceutically acceptable salt thereof as an active ingredient which comprises pulverizing a solid dispersion comprising the active ingredient and a glycolic acid-lactic acid copolymer having a weight-average molecular weight in the range from about 3,000 to about 30,000 and the ratio of lactic acid/glycolic acid is about 60/40 to 100/0 in the presence of a pulverizing auxiliary with or without (1) a water-soluble polymer and/or a nonionic surfactant (2) an amino acid as an antiaggregation agent,

(20) a method for producing a microparticle of (2R,4S)-(−)-N-[4-(diethoxyphosphorylmethyl)phenyl]-1,2,4,5-tetrahydro-4-methyl-7,8-methylenedioxy-5-oxo-3-benzothiepine-2-carboxamide or a pharmaceutically acceptable salt thereof which comprises pulverizing a solid dispersion comprising the active ingredient and glycolic acid/lactic acid copolymer having a weight-average molecular weight in the range from about 3,000 to about 30,000 and the ratio of lactic acid/glycolic acid is about 60/40 to 100/0 in the presence of a pulverizing auxiliary with either (1) a water-soluble polymer or surfactant, and/or (2) an antiaggregation agent, optionally followed by coating the resultant microparticle with the remaining of (1) or (2), and

(21) a method for producing a microparticle of (2R,4S)-(−)-N-[4-(diethoxyphosphorylmethyl)phenyl]-1,2,4,5-tetrahydro-4-methyl-7,8-methylenedioxy-5-oxo-3-benzothiepine-2-carboxamide or a pharmaceutically acceptable salt thereof which comprises pulverizing a solid dispersion comprising the active ingredient and glycolic acid/lactic acid copolymer having a weight-average molecular weight in the range from about 3,000 to about 30,000 and the ratio of lactic acid/glycolic acid is about 60/40 to 100/0 in the presence of a pulverizing auxiliary optionally followed by coating the resultant microparticle with (1) a water-soluble polymer and/or surfactant, and/or (2) an antiaggregation agent.

In the present invention, a compound of the formula (I):

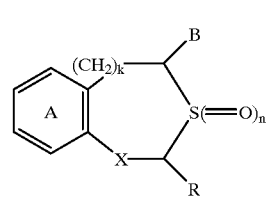

(I)

wherein ring A is an optionally substituted benzene ring; R is a hydrogen atom or an optionally substituted hydrocarbon group; B is an optionally esterified or amidated carboxyl group; X is —CH(OH)— or —CO—; k is 0 or 1; and n is 0, 1 or 2, or its pharmaceutically acceptable salt is used as an active ingredient.

With respect to the formula (I), the substituent of the substituted benzene represented by ring A is exemplified by halogen atoms, nitro groups, optionally substituted alkyl groups, optionally substituted hydroxyl groups, optionally substituted thiol groups, optionally substituted amino groups, acyl groups, mono- or di-alkoxyphosphoryl groups, phosphono groups, optionally substituted aryl groups, optionally substituted aralkyl groups and optionally substituted aromatic heterocyclic groups. Of these substituents, 1 to 4, preferably 1 or 2, whether identical or not, may be present on the benzene ring.

The halogen atoms include fluorine, chlorine, bromine and iodine.

The alkyl groups of the optionally substituted alkyl groups include alkyl groups having 1 to 10 carbon atoms ($C_{1-10}$ alkyl) such as methyl, ethyl, propyl, isopropyl, butyl, isobutyl, sec-butyl, tert-butyl, pentyl, isopentyl, neopentyl, hexyl, heptyl, octyl, nonyl and decyl, and $C_{3-7}$ cycloalkyl groups such as cyclopropyl, cyclobutyl, cyclohexyl and cycloheptyl. These alkyl groups may be substituted by 1 to 3 substituents selected from halogen atoms (e.g., fluorine, chlorine, bromine, iodine), hydroxyl groups, $C_{1-6}$ alkoxy groups (e.g., methoxy, ethoxy, propoxy, butoxy, hexyloxy), mono- or di-$C_{1-6}$ alkoxyphosphoryl groups (e.g. methoxyphosphoryl, ethoxyphosphoryl, dimethoxyphosphoryl, diethoxyphosphoryl) and phosphono groups.

The substituted alkyl groups include trifluoromethyl, trifluoroethyl, trichloromethyl, hydroxymethyl, 2-hydroxyethyl, methoxyethyl, 1-methoxyethyl, 2-methoxyethyl, 2,2-diethoxyethyl, 2-diethoxyphosphorylethyl, phosphonomethyl and so on.

The substituted hydroxyl groups include alkoxy groups, alkenyloxy groups, aralkyloxy groups, acyloxy groups, $C_{1-10}$ aryloxy groups and so on. Preferable alkoxy groups are alkoxy groups (e.g., methoxy, ethoxy, propoxy, butoxy, tert-butoxy, pentyloxy, hexyloxy, heptyloxy, nonyloxy) and $C_{4-6}$ cycloalkoxy groups (e.g., cyclobutoxy, cyclopentoxy, cyclohexyloxy). Preferable alkenyloxy groups are $C_{2-10}$ alkenyloxy groups such as allyloxy, crotyloxy, 2-pentenyloxy, 3-hexenyloxy, 2-cyclopentenylmethoxy and 2-cyclohexenylmethoxy. Preferable aralkyloxy groups are $C_{7-19}$ aralkyloxy groups, with greater preference given to $C_{6-14}$ aryl-$C_{1-4}$ alkyloxy groups (e.g., benzyloxy, phenethyloxy). Preferable acyloxy groups are alkanoyloxy groups such as those having 2 to 10 carbon atoms (e.g., acetyloxy, propionyloxy, n-butyryloxy, hexanoyloxy). Preferable aryloxy groups are $C_{6-14}$ aryloxy groups (e.g., phenoxy, biphenyloxy). Further, these groups may be substituted by 1 to 3 substituents selected from the above-mentioned halogen atoms, hydroxyl groups, $C_{1-6}$ alkoxy groups, mono- or di-$C_{1-6}$ alkoxyphosphoryl groups, etc. The substituted hydroxyl groups include trifluoromethoxy, 2,2,2-trifluoroethoxy, difluoromethoxy, 2-methoxyethoxy, 4-chlorobenzyloxy and 2-(3,4-dimethoxyphenyl)ethoxy, and so on.

The substituted thiol groups include alkylthio groups, aralkylthio groups and acylthio groups. Preferable alkylthio groups are $C_{1-10}$ alkylthio groups (e.g., methylthio, ethylthio, propylthio, butylthio, pentylthio, hexylthio, heptylthio, nonylthio) and $C_{4-6}$ cycloalkylthio groups (e.g., cyclobutylthio, cyclopentylthio, cyclohexylthio). Preferable aralkylthio groups are $C_{7-19}$ aralkylthio groups, more preferably $C_{6-14}$ aryl-$C_{1-4}$ alkylthio groups such as benzylthio and phenethylthio. Preferable acylthio groups are alkanoylthio groups such as those having 2 to 10 carbon atoms (e.g., acetylthio, propionylthio, n-butyrylthio, hexanoylthio). Further, these substituted thiol groups may be substituted by 1 to 3 substituents selected from the above-mentioned halogen atoms, hydroxyl groups, $C_{1-6}$ alkoxy groups, mono- or di-$C_{1-6}$ alkoxyphosphoryl groups etc. Specifically, the substituted thiol groups include trifluoromethylthio, 2,2,2-trifluoroethylthio, 2-methoxyethylthio, 4-chlorobenzylthio, 3,4-dichlorobenzylthio, 4-fluorobenzylthio, 2-(3,4-dimethoxyphenyl)ethylthio, and so on.

As substituents of the substituted amino groups, there may be used 1 or 2 identical or different substituents selected from the above-mentioned $C_{1-10}$ alkyl groups, $C_{2-10}$ alkenyl groups (e.g., allyl, vinyl, 2-penten-1-yl, 3-penten-1-yl, 2-hexen-1-yl, 3-hexen-1-yl, 2-cyclohexenyl, 2-cyclopentenyl, 2-methyl-2-propen-1-yl, 3-methyl-2-buten-1-yl), $C_{6-14}$ aryl groups (e.g. phenyl, naphthyl) and $C_{7-19}$ aralkyl groups (e.g. benzyl). These substituents may be substituted by the above-mentioned halogen atoms, $C_{1-6}$ alkoxy groups, mono- or di-$C_{1-6}$ alkoxyphosphoryl groups, phosphono groups, etc. Specifically, the substituted amino groups include methylamino, dimethylamino, ethylamino, diethylamino, dibutylamino, diallylamino, cyclohexylamino, phenylamino, N-methyl-N-phenylamino, N-methyl-N-(4-chlorobenzyl)amino and N,N-di(2-methoxyethyl)amino, and so on.

The acyl groups include organic carboxylic acid acyl groups and sulfonic acid acyl groups with a $C_{1-6}$ hydrocarbon group (e.g., methyl, ethyl, n-propyl, hexyl, phenyl). Useful organic carboxylic acyl groups are formyl, $C_{1-10}$ alkyl-carbonyl groups (e.g., acetyl, propionyl, butyryl, valeryl, pivaloyl, hexanoyl, octanoyl, cyclobutanecarbonyl, cyclohexanecarbonyl, cycloheptanecarbonyl), $C_{2-10}$ alkenyl-carbonyl groups (e.g., crotonyl, 2-cyclohexenecarbonyl), $C_{6-14}$ aryl-carbonyl groups (e.g., benzoyl), $C_{7-19}$ aralkyl-carbonyl groups (e.g., benzylcarbonyl, benzhydrylcarbonyl), 5- or 6-membered aromatic heterocyclic carbonyl groups (e.g, nicotinoyl, 4-thiazolylcarbonyl) and 5- or 6-membered aromatic heterocyclic acetyl groups (e.g., 3-pyridylacetyl, 4-thiazolylacetyl). Useful $C_{1-6}$ sulfonic acyl groups are methanesulfonyl and ethanesulfonyl. These acyl groups may be substituted by 1 to 3 substituents selected from the above-mentioned halogen atoms, hydroxyl groups, $C_{1-6}$ alkoxy groups, amino groups, etc. Specifically, the substituted acyl groups include trifluoroacetyl, trichloroacetyl, 4-methoxybutyryl, 3-cyclohexyloxypropionyl, 4-chlorobenzoyl and 3,4-dimethoxybenzoyl, and so on.

The mono- or di-alkoxyphosphoryl groups include mono-$C_{1-6}$ alkoxyphosphoryl groups such as methoxyphosphoryl, ethoxyphosphoryl, propoxyphosphoryl, isopropoxyphosphoryl, butoxyphosphoryl, pentyloxyphosphoryl and hexyloxyphosphoryl, and di-$C_{1-6}$ alkoxyphosphoryl groups such as dimethoxyphosphoryl, diethoxyphosphoryl, dipropoxyphosphoryl, diisopropoxyphosphoryl, dibutoxyphosphoryl, dipentyloxyphosphoryl and dihexyloxyphosphoryl, with preference given to di-$C_{1-6}$ alkoxyphosphoryl groups such as dimethoxyphosphoryl, diethoxyphosphoryl, dipropoxyphosphoryl, diisopropoxyphosphoryl, ethylenedioxyphosphoryl, dibutoxyphosphoryl, etc.

The aryl groups of the optionally substituted aryl groups include $C_{6-14}$ aryl groups such as phenyl, naphthyl and anthryl. These aryl groups may be substituted by 1 to 3 substituents selected from the above-mentioned $C_{1-10}$ alkyl groups, halogen atoms, hydroxyl groups, $C_{1-6}$ alkoxy groups, etc. Specifically, the substituted aryl groups include 4-chlorophenyl, 3,4-dimethoxyphenyl, 4-cyclohexylphenyl and 5,6,7,8-tetrahydro-2-naphthyl.

The aralkyl groups of the optionally substituted aralkyl groups include $C_{7-19}$ aralkyl groups such as benzyl, naphthylethyl and trityl. These aralkyl groups may be substituted by 1 to 3 substituents selected from the above-mentioned $C_{1-10}$ alkyl groups, halogen atoms, hydroxyl groups, $C_{1-6}$ alkoxy groups etc. on the aromatic ring. Specifically, the substituted aralkyl groups include 4-chlorobenzyl, 3,4-dimethoxybenzyl, 4-cyclohexylbenzyl and 5,6,7,8-tetrahydro-2-naphthylethyl.

The aromatic heterocyclic groups of the optionally substituted aromatic heterocyclic groups include 5- to 6-membered aromatic heterocyclic groups having 1 to 4 atoms of nitrogen, oxygen and/or sulfur, such as furyl, thienyl, imidazolyl, thiazolyl, oxazolyl and thiadiazolyl. These aromatic heterocyclic groups may be substituted by 1 to 3 substituents selected from the above-mentioned $C_{1-10}$ alkyl groups, halogen atoms, hydroxyl groups, $C_{1-6}$ alkoxy groups, etc.

Provided that two alkyl groups are present as mutually adjoining substituents on the benzene ring A, they may bind together to form an alkylene group represented by the formula: —$(CH_2)_m$— wherein m is an integer from 3 to 5 (e.g., trimethylene, tetramethylene, pentamethylene). Provided that two alkoxy groups are present as mutually adjoining substituents on the benzene ring A, they may bind together to form an alkylenedioxy group represented by the formula: —O—$(CH_2)_q$—O— wherein q is an integer from 1 to 3 (e.g., methylenedioxy, ethylenedioxy, trimethylenedioxy). In these cases, a 5- to 7-membered ring is formed in cooperation with carbon atoms of the benzene ring.

With respect to the formula (I), R is a hydrogen atom or an optionally substituted hydrocarbon group.

The hydrocarbon group of the optionally substituted hydrocarbon group represented by R is exemplified by the above-mentioned alkyl groups (preferably $C_{1-10}$ alkyl groups), alkenyl groups (preferably $C_{2-10}$ alkenyl groups), aryl groups (preferably $C_{6-14}$ aryl groups) and aralkyl groups (preferably $C_{7-19}$ aralkyl groups). Useful substituents on the hydrocarbon group include the above-mentioned 5- or 6-membered aromatic heterocyclic groups, halogen atoms, di-$C_{1-6}$ alkoxyphosphoryl groups and phosphono groups.

Preferable examples of R are an unsubstituted $C_{1-6}$ alkyl groups such as methyl, ethyl, propyl, isopropyl, butyl, isobutyl, sec-butyl, tert-butyl, pentyl, neopentyl and hexyl.

With respect to the formula (I), B is an optionally esterified or amidated carboxyl group.

The esterified carboxyl group represented by B is exemplified by alkoxycarbonyl group, preferably $C_{1-10}$ alkoxycarbonyl groups (e.g., methoxycarbonyl, ethoxycarbonyl, propoxycarbonyl, butoxycarbonyl), aryloxy-carbonyl groups, preferably $C_{6-14}$ aryloxy-carbonyl groups (e.g., phenoxycarbonyl), and aralkyloxycarbonyl groups, preferably $C_{7-19}$ aralkyloxy-carbonyl groups (e.g., benzyloxycarbonyl).

The amidated carboxyl group represented by B is exemplified by an optionally substituted carbamoyl group represented by the formula: —$CON(R^4)(R^5)$ wherein $R^4$ and $R^5$ independently are a hydrogen atom, an optionally substituted hydrocarbon group or an optionally substituted 5- to 7-membered heterocyclic group.

The hydrocarbon group of the optionally substituted hydrocarbon group represented by $R^4$ or $R^5$ is exemplified by the above-mentioned alkyl groups, preferably $C_{1-10}$ alkyl groups (e.g., methyl, ethyl, propyl, isopropyl, butyl, isobutyl, sec-butyl, tert-butyl, pentyl, isopentyl, neopentyl, hexyl, heptyl, octyl, nonyl, decyl), alkenyl groups, preferably $C_{2-10}$ alkenyl groups (e.g., allyl, vinyl, 2-penten-1-yl, 3-penten-1-yl, 2-hexen-1-yl, 3-hexen-1-yl, 2-cyclohexenyl, 2-cyclopentenyl, 2-methyl-2-propen-1-yl, 3-methyl-2-buten-1-yl), aryl groups, preferably $C_{6-14}$ aryl group (e.g., phenyl, naphthyl, anthryl), and aralkyl groups, preferably $C_{7-19}$ aralkyl group (e.g., benzyl, naphthyl, trityl). These hydrocarbon groups may be substituted by 1 to 3 substituents selected from (i) halogen atoms (e.g., fluorine, chlorine, bromine, iodine), (ii) hydroxyl groups, (iii) $C_{1-6}$ alkoxy groups (e.g., methoxy, ethoxy, propoxy, butoxy, tert-butoxy, pentyloxy, hexyloxy), (iv) amino groups which may be substituted by $C_{1-6}$ alkyl groups (e.g., methyl, ethyl, propyl, isopropyl, butyl, isobutyl, sec-butyl, pentyl, isopentyl, neopentyl, hexyl, etc.) (e.g., amino, methylamino, ethylamino, dimethylamino, diethylamino, dipropylamino), (v) amino groups substituted by acyl groups such as $C_{1-10}$ alkanoyl groups (e.g., acetylamino, propionylamino, benzoylamino), (vi) carbamoyl groups which may be substituted by $C_{1-6}$ alkyl groups (e.g., carbamoyl, methylcarbamoyl, dimethylcarbamoyl, diethylcarbamoyl), (vii) $C_{1-6}$ alkoxy-carbonyl groups (e.g., methoxycarbonyl, ethoxycarbonyl, propoxycarbonyl), (viii) mono- or di-alkoxyphosphoryl groups (e.g. mono- or di-$C_{1-6}$ alkoxyphosphoryl groups such as dimethoxyphosphoryl, diethoxyphosphoryl, ethylenedioxyphosphoryl), (ix) mono- or di-alkoxyphosphorylalkyl groups (e.g. mono- or di-$C_{1-6}$ alkoxyphosphoryl-$C_{1-3}$ alkyl groups such as methoxyphosphorylmethyl, ethoxyphosphorylmethyl, methoxyphosphorylethyl, ethoxyphosphorylethyl, dimethoxyphosphorylmethyl, diethoxyphosphorylmethyl, dimethoxyphosphoryethyl, diethoxyphosphoryethyl), (x) a moiety represented by the formula:

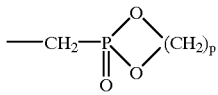

wherein p is an integer from 2 to 4, (xi) phosphono groups, (xii) aromatic heterocyclic groups (the same meaning mentioned above), etc.

The 5- to 7-membered heterocyclic group of the optionally substituted 5- to 7-membered heterocyclic group represented by $R^4$ or $R^5$ is exemplified by 5- to 7-membered heterocyclic groups containing a sulfur, nitrogen or oxygen atom, 5- or 6-membered heterocyclic groups containing 2 to 4 nitrogen atoms, and 5- or 6-membered heterocyclic groups containing 1 or 2 nitrogen atom(s) and a sulfur or oxygen atom. These heterocyclic groups may be condensed with a 6-membered ring containing 2 or fewer nitrogen atoms, a benzene ring or a 5-membered ring containing a sulfur atom.

As substituents of the substituted 5- to 7-membered heterocyclic group represented by $R^4$ and $R^5$, there may be used 1 to 4 of the same substituents as those for the substituted hydrocarbon group represented by $R_1$ and $R_2$ above.

Preferable examples of the 5- to 7-membered heterocyclic group represented by $R^4$ and $R^5$ include 2-pyridyl, pyrimidyl, pyrazinyl, pyridazinyl, pyrazolyl, imidazolyl, thiazolyl, oxazolyl, pyrido[2,3-d]pyrimidyl, benzopyranyl, 1,8-naphthyridyl, quinolyl, thieno[2,3-b]pyridyl, tetrazolyl, thiadiazolyl, oxadiazolyl, triazinyl, triazolyl, thienyl, pyrrolyl, pyrrolinyl, furyl, pyrrolidinyl, benzothienyl, indolyl, imidazolidinyl, piperidyl, piperidino, piperazinyl, morpholinyl and morpholino.

The moiety: —$NR^4(R^5)$ may form a 5- to 7-membered ring by binding together with $R^4$ and $R^5$. Such rings include morpholine, piperidine, thiomorpholine, homopiperidine, piperidine, pyrrolidine, thiazolidine and azepine.

The substituted alkyl groups as preferable examples of the optionally substituted hydrocarbon group represented by $R^4$ and $R^5$ include trifluoromethyl, trifluoroethyl, difluoromethyl, trichloromethyl, 2-hydroxyethyl, 2-methoxyethyl, 2-ethoxyethyl, 2,2-dimethoxyethyl, 2,2-diethoxyethyl, 2-pyridylmethyl, 3-pyridylmethyl, 4-pyridylmethyl, 2-(2-thienyl)ethyl, 3-(3-furyl)propyl, 2-morpholinoethyl, 3-pyrrolylbutyl, 2-piperidinoethyl, 2-(N,N-dimethylamino)ethyl, 2-(N-methyl-N-ethylamino) ethyl, 2-(N,N-diisopropylamino)ethyl, 5-(N,N-dimethylamino)pentyl, N,N-dimethylcarbamoylethyl, N,N-dimethylcarbamoylpentyl, ethoxycarbonylmethyl, isopropoxycarbonylethyl, tert-butoxycarbonylpropyl, 2-diethoxyphosphorylethyl, 3-dipropoxyphosphorylpropyl, 4-dibutoxyphosphorylbutyl, ethylenedioxyphosphorylmethyl, 2-phosphonoethyl and 3-phosphonopropyl. The preferable substituted aralkyl groups include 4-chlorobenzyl, 3-(2-fluorophenyl)propyl, 3-methoxybenzyl, 3,4-dimethoxyphenethyl, 4-ethylbenzyl, 4-(3-trifluoromethylphenyl)butyl, 4-acetylaminobenzyl, 4-dimethylaminophenethyl, 4-diethoxyphosphorylbenzyl and 2-(4-dipropoxyphosphorylmethylphenyl)ethyl. The preferable substituted aryl groups include 4-chlorophenyl, 4-cyclohexylphenyl, 5,6,7,8-tetrahydro-2-naphthyl, 3-trifluoromethylphenyl, 4-hydroxyphenyl, 3,4,5-trimethoxyphenyl, 6-methoxy-2-naphthyl, 4-(4-chlorobenzyloxy)phenyl, 3,4-methylenedioxyphenyl, 4-(2,2,2-trifluoroethoxy)phenyl, 4-propionylphenyl, 4-cyclohexanecarbonylphenyl, 4-dimethylaminophenyl, 4-benzoylaminophenyl, 4-diethoxycarbamoylphenyl, 4-tert-butoxycarbonylphenyl, 4-diethoxyphosphorylphenyl, 4-diethoxyphosphorylmethylphenyl, 4-(2-diethoxyphosphorylethyl)phenyl, 2-diethoxyphosphorylmethylphenyl, 3-diethoxyphosphorylmethylphenyl, 4-dipropoxyphosphorylphenyl, 4-(2-phosphonoethyl) phenyl, 4-phosphonomethylphenyl and 4-phosphonophenyl. The preferable substituted 5- to 7-membered heterocyclic groups include 5-chloro-2-pyridyl, 3-methoxy-2-pyridyl, 5-methyl-2-benzothiazolyl, 5-methyl-4-phenyl-2-thiazolyl, 3-phenyl-5-isoxazolyl, 4-(4-chlorophenyl)-5-methyl-2-oxazolyl, 3-phenyl-1,2,4-thiadiazol-5-yl, 5-methyl-1,3,4-thiadiazol-2-yl, 5-acetylamino-2-pyrimidyl, 3-methyl-2-thienyl, 4,5-dimethyl-2-furanyl and 4-methyl-2-morpholinyl.

With respect to the formula (I), ring A is preferably a benzene ring which may be substituted by 1 or more, more preferably 1 or 2 substituents selected from ① halogen atoms, ② optionally substituted alkyl groups, ③ optionally substituted hydroxyl groups, ④ optionally substituted thiol groups and/or ⑤ optionally substituted amino groups.

More preferably, ring A is a benzene ring which may be substituted by 1 or 2 substituents selected from the above-mentioned halogen atoms, $C_{1-10}$ alkyl groups (furthermore preferably $C_{1-5}$ alkyl groups), $C_1$ alkoxy groups (furthermore preferably $C_{1-5}$ alkoxy groups), alkylenedioxy groups represented by the formula: —O—$(CH_2)_q$—O— wherein q is an integer from 1 to 3, and/or $C_{1-10}$ alkylthio groups (furthermore preferably $C_{1-5}$ alkylthio groups).

Most preferably, ring A is a benzene ring which may be substituted by an alkylenedioxy group represented by the formula: —O—$(CE_2)_q$—O— wherein q is an integer from 1 to 3.

B is preferably an alkoxy-carbonyl group or a group represented by the formula: —$CON(R^4)(R^5)$ wherein $R^4$ and $R^5$ independently are a hydrogen atom, an optionally substituted hydrocarbon group or an optionally substituted 5- to 7-membered heterocyclic group.

With respect to $R^4$ and $R^5$ above, $R^4$ is preferably a hydrogen atom or a $C_{1-10}$ alkyl group (e.g. methyl, ethyl, propyl), and $R^5$ is preferably a phenyl or phenyl-$C_{1-3}$ alkyl group which may be substituted by a halogen atom (e.g. fluorine, chlorine, bromine), a $C_{1-6}$ alkoxy (e.g. methoxy, ethoxy), a mono- or di-alkoxyphosphoryl (preferablly a mono- or di-$C_{1-6}$ alkoxyphosphoryl such as diethoxyphosphoryl), a mono- or di-alkoxyphosphorylalkyl (preferablly a mono- or di-$C_{1-6}$ alkoxyphosphoryl-$C_{1-3}$ alkyl such as diethoxyphosphoryl-methyl) or a $C_{1-6}$ alkoxycarbonyl (e.g. methoxycarbonyl, ethoxycarbonyl), or a 5- or 6-membered heterocyclic group (e.g. pyridyl) which may be substituted by a phenyl and that contains 1 or 2 nitrogen atom(s) or a nitrogen atom and a sulfur atom.

More preferably, $R^4$ is a hydrogen atom, and $R^5$ is a phenyl group substituted by a mono- or di-$C_{1-6}$ alkoxyphosphoryl-$C_{1-3}$ alkyl (e.g. 4-diethoxyphosphorylmethylphenyl).

With respect to the formula (I), X is —CH(OH)— or —CO—, preferably —CO—.

With respect to the formula (I), k is 0 or 1, and n is 0, 1 or 2, preferablly k is 1, and n is 0.

R is preferably a hydrogen atom, a $C_{1-6}$ alkyl group (e.g. methyl, ethyl) or a phenyl group.

The compound (I) is preferably an optically active compound represented by the formula (II):

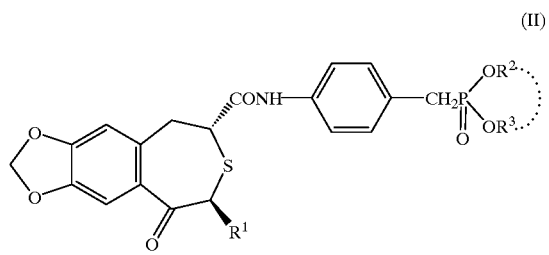

(II)

wherein $R^1$ is a hydrogen atom or an optionally substituted hydrocarbon group; $R^2$ and $R^3$ independently are a lower alkyl group or bind together to form a lower alkylene group.

In the formula (II) above, the optionally substituted hydrocarbon group represented by $R^1$ is the same meanings as the above-mentioned hydrocarbon groups represented by R. Among them unsubstituted $C_{1-6}$ alkyl groups such as methyl, ethyl, propyl, isopropyl, butyl, isobutyl, sec-butyl, tert-butyl, pentyl, isopentyl, neopentyl and hexyl. $C_{1-4}$ alkyl groups is most preferable.

The lower alkyl group represented by $R^2$ or $R^3$ is exemplified by $C_{1-6}$ alkyl groups (preferably $C_{1-4}$ alkyl group) such as methyl, ethyl, propyl, isopropyl, butyl, isobutyl, sec-butyl, tert-butyl, pentyl, isopentyl, neopentyl and hexyl. $R^2$ and $R^3$ may bind together to form a lower alkylene group. In this case, a moiety:

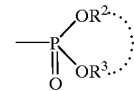

may represent a moiety:

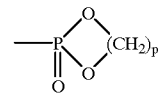

wherein p is an integer from 2 to 4.

Preferable groups for $R^1$, $R^2$ and $R^3$ include alkyl groups having 1 to 4 carbon atoms such as methyl and ethyl.

The compound represented by (II) (hereinafter sometimes referred to as compound (II)) is an optically active compound of the (2R,4S) configuration, and contains substantially no compound of the (2S,4R) configuration. The compound (II) of which optical purity is nearly 100% is preferable.

The salt of the compound used in the present invention is preferably a pharmaceutically acceptable salt. Examples of pharmaceutically acceptable salts include salts with inorganic bases, salts with organic bases and salts with basic or acidic amino acids. Examples of the inorganic bases capable of forming such salts include alkali metals (e.g., sodium, potassium) and alkaline earth metals (e.g., calcium, magnesium) and examples of the organic bases include trimethylamine, triethylamine, pyridine, picoline, N,N-dibenzylethylenediamine and diethanolamine, examples of the inorganic acids include hydrochloric acid, hydrobromic acid, hydroiodic acid, phosphoric acid, nitric acid and sulfuric acid, examples of the organic acids include formic acid, acetic acid, trifluoroacetic acid, oxalic acid, tartaric acid, fumaric acid, maleic acid, methanesulfonic acid, benzenesulfonic acid, p-toluenesulfonic acid and citric acid, and examples of the basic or acidic amino acids include arginine, lysine, aspartic acid and glutamic acid.

Most preferably, the compound (II) is, for example, (2R,4S)-(–)-N-[4-(diethoxyphosphorylmethyl)phenyl]-1,2,4,5-tetrahydro-4-methyl-7,8-methylenedioxy-5-oxo-3-benzothiepine-2-carboxamide (hereinafter also referred to as compound A).

The preferable examples of the present invention include the osteogenesis-promoting compounds disclosed in Japanese laid-open patent applications 232880/1991 (corresponding to EP-A-0376197), 364179/1992 (corresponding to EP-A-0460488), 294960/1994, etc. or a salt thereof (e.g. (2R,4S)-(–)-N-(4-(diethoxyphosphorylmethyl)phenyl]-1,2,4,5-tetrahydro-4-methyl-7,8-methylendioxy-5-oxo-3-benzothiepine-2-carboxamide) and benzothiepine derivatives specifically disclosed in Japanese laid-open application 231569/1996 (corresponding to EP-A-0719782), These compounds may be used in a combination of two or more kinds in an appropriate ratio.

The compound represented by the formula (I) for the present invention can be produced by the method described in the above patent publications or a modification thereof.

The biodegradable polymer of α-hydroxycarboxylic acid in the present invention includes a homopolymer, a copolymer of α-hydroxycarboxylic acid represented by the formula:

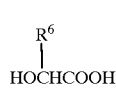

[III]

wherein $R^6$ represents a hydrogen atom or an alkyl group having 1 to 8 carbon atoms; or a mixture thereof.

With respect to the formula [III] above, the linear or branched $C_{1-8}$ alkyl group represented by $R^6$ is exemplified by methyl, ethyl, propyl, isopropyl, butyl, isobutyl, sec-butyl, tert-butyl, pentyl, isopentyl, neopentyl, tert-pentyl, 1-ethylpropylt hexyl, isohexyl, 1,1-dimethylbutyl, 2,2-dimethylbutyl, 3,3-dimethylbutyl and 2-ethylbutyl. Preferably, a linear or branched $C_{2-5}$ alkyl group is used. Such alkyl groups include ethyl, propyl, isopropyl, butyl and isobutyl.

The preferable embodiments of hydroxycarboxylic acid represented by the formula [III] is exemplified by glycolic acid, lactic acid, 2-hydroxybutyric acid, 2-hydroxyvaleric acid, 2-hydroxy-3-methylbutyric acid, 2-hydroxycaproic acid, 2-hydroxyisocaproic acid and 2-hydroxycapric acid, with preference given to glycolic acid, lactic acid, 2-hydroxy-butyric acid, 2-hydroxyvaleric acid, 2-hydroxy-3-methyl-butyric acid and 2-hydroxycaproic acid. When optical isomers of these α-hydroxycarboxylic acid exist, any one of D-isomer, L-isomer and racemic mixtures thereof may be used.

The hydroxycarboxylic acid represented by the formula [III] may be used as a mixture of one or more kinds in a given ratio.

With respect to the copolymer produced from 2 or more kinds of the α-hydroxycarboxylic acid represented by the formula [III], polymerization may be of random, block or graft type. A random copolymer is preferred.

With respect to the copolymer produced from 2 or more kinds of the α-hydroxycarboxylic acid represented by the formula [III], polymerization may be of random, block or graft type. A random copolymer is preferred.

The polymer of single kind of the α-hydroxycarboxylic acid represented by the formula [III], in the case of the α-hydroxycarboxylic acid having an optical isomer, although it may be of the D- or L-configuration or a mixture thereof, it is preferable that the ratio of the D-/L-configuration (mol %) falls within the range from about 75/25 to about 20/80. The ratio of the D-/L-configuration (mol %) is more preferably about 60/40 to about 25/75, and still more preferably about 55/45 to about 25/75. The weight-average molecular weight of the polymer is preferably within the range from about 1,500 to about 30,000, more preferably about 2,000 to about 20,000, and still more preferably about 3,000 to about 15,000. Also, the degree of dispersion of the polymer is preferably about 1.2 to about 4.0, more preferably about 1.5 to about 3.5.

For producing the above polymers, the methods: ring-opening polymerization of a dimer of the α-hydroxycarboxylic acid (e.g. glycolide, lactide etc., and dehydration polycondensation of the α-hydroxycarboxylic acid) are known. For obtaining a polymer of relatively low molecular weight for the present invention, direct dehydration polycondensation of the α-hydroxycarboxylic acid represented by the formula (III) is preferred. This method is, for example, described in Japanese Patent Unexamined Publication No. 28521/1986.

The α-hydroxycarboxylic acid singly used for polymerization is preferably glycolic acid, lactic acid, 2-hydroxybutyric acid, more preferably lactic acid.

The preferable examples of the above-mentioned copolymers include copolymers of glycolic acid and lactic acid (glycolic acid/lactic acid copolymers) and copolymers of glycolic acid and a α-hydroxycarboxylic acid represented by the formula [III] wherein $R^6$ is $C_{2-8}$ alkyl group (e.g. ethyl, propyl, isopropyl, butyl, isobutyl, hexyl, 2,2-dimethylbutyl, 2-ethylbutyl, etc.) (hereinafter referred to as glycolic acid copolymer). Glycolic acid/lactic acid copolymers and copolymers of glycolic acid and 2-hydroxycarboxylic acid are more preferable.

With respect to the content ratio of lactic acid and glycolic acid of the lactic acid/glycolic acid copolymer, lactic acid preferably accounts for about 40 to about 95 mol % and glycolic acid preferably accounts for about 60 to about 5 mol %, more preferably lactic acid accounts for about 50 to about 95 mol % and glycolic acid accounts for about 50 to about 5 mol %, even more preferably lactic acid accounts for about 60 to about 90 mol % and glycolic acid accounts for about 40 to about 10 mol %.

The weight-average molecular weight of the lactic acid/glycolic acid copolymer used in the present invention is preferably about 1,000 to about 100,000, more preferably about 2,000 to about 50,000, still more preferably about 5,000 to about 30,000.

The degree of dispersion of the lactic acid/glycolic acid copolymer (weight-average molecular weight/number-average molecular weight) is preferably about 1.2 to about 4.0, more preferably about 1.5 to about 3.5.

With respect to the content ratio of glycolic acid and the hydroxycarboxylic acid represented by the formula [III] wherein $R^6$ is $C_{2-8}$ alkyl group in the above glycolic acid copolymer, it is preferable that glycolic acid accounts for about 10 to 75 mol % and hydroxycarboxylic acid accounts for the remaining portion. More preferably, glycolic acid accounts for about 20 to about 75 mol %, and still more preferably about 40 to about 70 mol %. The weight-average molecular weight of the glycolic acid copolymer is normally about 2,000 to about 50,000, preferably about 3,000 to about 40,000, and more preferably about 8,000 to about 30,000. The degree of dispersion of the glycolic acid copolymer is preferably about 1.2 to about 4.0, more preferably about 1.5 to about 3.5.

The glycolic acid/lactic acid copolymer and the glycolic acid copolymer above can be produced by known processes, such as that described in Japanese laid-open application No. 28521/1986 or a method similar thereto.

The polymers of α-hydroxycarboxylic acid used as a microparticle base in the production method of the present invention can be produced by the known method, such as described in Japanese laid-open applications 157525/1975, 45920/1981, 118512/1982, 150609/1982 and 54760/1987 and EP-A-048/732 or modification thereof other than those described above.

In the present specification, weight-average molecular weight and degree of dispersion are defined as the molecular weight based on polystyrene obtained by gel permeation chromatography (GPC) with 9 polystyrenes as reference substances with respective weight-average molecular weights of 120,000, 52,000, 22,000, 9,200, 5,050, 2,950, 1,050, 580 and 162, and degree of dispersion calculated respectively. Measurements were taken using a GPC column KF804L×2 (produced by Showa Denko, Japan) and an RI monitor L-3300 (produced by Hitachi, Ltd., Japan) with chloroform as the mobile phase.

The preferable examples of the mixture of homopolymer or copolymer of the α-hydroxycarboxylic acid represented by the formula [III] include mixtures of the above described glycolic acid copolymer (A) and a polylactic acid (B) in an appropriate ratio.

The glycolic acid copolymer (A) and the polylactic acid (B) are used in the mixture wherein the (A)/(B) ratio (% by weight) falls within the range from about 10/90 to about 90/10. The mixing ratio is preferably about 20/80 to about 80/20, and more preferably about 30/70 to about 70/30. If either component (A) or (B) is in excess to such a large extent, the preparation obtained shows a drug release pattern almost the same as that which is obtained with the use of either component (A) or (B) alone and no linear release pattern is expected in the last stage of drug release from the mixed base. Although the decomposition/elimination rates of glycolic acid copolymer (A) and polylactic acid (B) vary widely, depending on molecular weight or composition, drug release duration can be extended by increasing the molecular weight of the polylactic acid or lowering the mixing ratio (A)/(B), since the decomposition/elimination rate of glycolic acid copolymer is usually higher than that of polylactic acid. Conversely, drug release duration can be shortened by decreasing the molecular weight of polylactic acid or increasing the mixing ratio (A)/(B). Drug release duration can also be adjusted by altering the kind and content ratio of α-hydroxycarboxylic acid represented by the formula [III].

In the production method of the present invention, the solid preparation comprising the compound represented by the formula [I] and a biodegradable polymer of α-hydroxycarboxylic acid can be produced by the method which comprises dissolving (a) a compound represented by the formula [I] and (b) a biodegradable polymer of α-hydroxycarboxylic acid in a solvent which could dissolve (a) and (b) together, followed by drying the solution under the reduced pressure or a method analogous thereto. Any method may be used for preparing the solution of (a) and (b), as long as (a) and (b) are finally dissolved in the solvent. The method includes for example (1) mixing a solution or suspension of (a) with a solution or a suspension of (b), (2) mixing a solution or suspension of (a) in the solvent with (b), (3) mixing a solution or suspension of (b) in a solvent with (a) or (4) dissolving a mixture of (a) and (b) into the solvent. As the solvent, any solvent that can disolve both (a) and (b) by mixing to give a solution of (a) and (b) may be properly selected.

The solvent which can dissolve (a) and (b) together may be any solvent as long as (a) and (b) are finally dissolved thereinto. Specific examples of the solvent, include a halogenated hydrocarbon or a mixture of two or more kinds thereof in appropriate ratios, to which opptionally, an aprotic solvent and/or a lower alcohol may be added if necessary in such an amount as not to inhibit dissolution of (a) or (b). Halogenated hydrocarbons such as methylene chloride, chloroform and dichloromethane and aprotic solvents such as acetonitrile, acetone and dioxane are preferably used. The solvent may be a mixture of two or more kinds of these organic solvents in an appropriate ratio. Further, lower alcohols such as methanol, ethanol, propanol and the like may be added into the solvent in such an amount as not to inhibit the dissolution of (a) and (b).

In the preparation of the solution of (a) and (b), a surfactant may be added if necessary. As the surfactant, examples mentioned below can be used.

The amount of the compound represented by the formula [III] to be used for the preparation may be changed according to kind, continuation period of effect of drug etc. The concentration in the solution may be chosen within the range from about 0.001% (w/w) to about 15% (w/w), preferably from about 0.01% to about 10% (w/w).

The amount of the biodegradable polymer of α-hydroxycarboxylic acid to be used for the preparation may be selected according to rate or duration of drug release. For example, while a range from about 0.5 to 10,000-fold can be used, preferably from about 1 to about 100-fold, ratio by weight of the polymers relative to the active ingredient of a benzothiepin derivative are used.

The method for drying under the reduced pressure may be carried out according to the per se known manner.

With respect to the reduced pressure used herein, it is preferably less than about 400 Torr, more preferably less than about 300 Torr.

The temperature for drying is preferably within the range from about 10° C. to about 70° C., more preferably within the range from about 15 to about 50° C.

The reaction time of this step is preferably about 1 hour to about 72 hours, more preferably about 1 hour to about 48 hours.

In the present invention, microparticles are produced by pulverizing thus obtained solid preparation in the presence of a pulvilizing auxiliary. The pulverization may be carried out according to a per se known pulverizing manner. For example, the pulverization is done by using a conventional pulverizer such as a turbo counter jet mill or a ultrasonic jet mill.

In this step, usually, the solid preparation is roughly ground into coarse particles before subjecting to the pulverizer, since this is convenient for increasing the efficiency of pulverization. Such rough grind is done by using mortar or conventional pulverizer such as power mill. With respect to the size of the coarse particles, it may be chosen based on the pulverization condition such as type of pulverizer or the requirements of the object microparticles such as particle size, from the range of the particle diameter up to about 4 mm, preferably up to about 2 mm, more preferably from about 1 mm to about 2 mm.

In the pulverization, the size of the microparticles may be chosen based on the administration route or requirements of the final product etc. When the microcapsules are used as an injectable suspension, for instance, their particle size is chosen over the range preferably from about 0.5 to about 400 μm of average particle diameter, as long as the requirements concerning the degree of dispersion and needle passage are met. More preferably, the average particle diameter is about 2 to about 200 μm.

In the above pulverizing step, it is useful for preventing aggregation of the microparticles during the pulverization or storage period to add an antiaggregation agent (an agent which prevents aggregation, coagulation or flocculation) to the subjects and pulverize it with them according to necessity.

The antiaggregation agent may be added to the microparticles and mixed by the mixer after pulverization.

As the pulverizing auxiliary is generally a substance which is soluble in water, in a solid form under the pulverizing condition and has a hardness higher than that of the solid preparation to be pulverized. The larger the difference in the hardness between the pulverizing auxiliary and the subject to be pulverized, the more preferable to use it is. The pulverizing auxiliary is preferably a crystal or a crystalline compound.

Specific examples of the pulverizing auxiliary include inorganic salts such as halogenated alkali metals (e.g. (1)

sodium chloride, potassium chloride, sodium bromide, potassium bromide), halogenated alkali earth metals (e.g. calcium chloride, magnesium chloride), phosphate salt of alkali metals (e.g. tribasic sodium phosphate, tribasic potassium phosphate, dibasic sodium phosphate, dibasic potassium phosphate, monobasic sodium phosphate, monobasic potassium phosphate), alkali earth metal oxides (e.g. magnesium oxide, calcium oxide) and alkali earth metal hydroxide (e.g. magnesium hydroxide, calcium hydroxide); (2) organic acids or salts thereof such as carbonic acid, citric acid, carbonate or bicarbonate salt of alkali metals (e.g. sodium carbonate, potassium carbonate, sodium bicarbonate, potassium bicarbonate), carbonate salt of alkali earth metals (e.g. calcium carbonate, magnesium carbonate), citrate salts of alkali metals; (3) saccharides such as sugar alcohols (e.g. mannitol, sorbitol), monosaccharides (e.g. glucose, galactose), disaccharides (e.g. lactose, sucrose, maltose), amino sugars (e.g. glucosamine, galactosamine, chondroitin phosphate) and polysaccharides (e.g. dextrine, hydroxypropyl cellulose). These pulverizing auxiliaries may be used in combination of one or more kinds in appropriate ratio. Among them, inorganic salts and water-soluble saccharides are preferable.

It is also in the scope of the present invention to use ice ($H_2O$) as a pulverizing auxiliary in addition to ones described above when pulverization is conducted at a low temperature not higher than the freezing point.

The amount of the pulverizing auxiliary to be used may be selected within the range from about 0.001 to about 100 fold by weight relative to the solid preparation based on the average particle diameter of the desired microparticles, particle diameter apt to be smaller according to increase of the content ratio of the pulverizing auxiliary in the same pulverizing condition.

The particle size of the pulverizing auxiliary subjected to the pulverizer is appropriately selected from the range of average particle size based on weight distribution from about 0.5 μm to about 2000 μm depending on the particle diameter of the desired microparticles. The particle size of the microparticles produced in this manner can be controlled by choosing the kind of content ratio and average particle diameter of pulverizing auxiliary.

One of the preferable embodiments of the pulverization in case of pulverizing the solid preparation into microparticles having average particle size from about 10 to about 50 μm by using supersonic jet mill (PJM-100SP NIPPON PNEUMATIC MFG CO. LTD.), is exemplified below.

The solid dispersion (preferably solid solution) roughly ground into coarse particles having particle diameter not more than 2 mm is mixed with about 3 to about 50% (w/w) pulverizing auxiliary relative thereto. The resulting mixture is pulverized by the supersonic jet mill under pressure within a range from about 0.05 MPa to 0.5 MPa while supplying of the subject mixture in a rate of about 30 g/min to about 120 g/min.

The pulverizing auxiliary can be removed after pulverization, if necessary, by washing with water or using known separation manner based on the difference of the particle size. The freeze-drying method is also a useful removing method, when ice is used as the pulverizing auxiliary.

If necessary, the dispersion ability of the microparticle to dispersion solvent can be improved by coating its surface with a water-soluble polymer and/or a surfactant which are soluble in water, administerable to human being and in a solid form at ordinary temperature (about 15–25° C.). Meanings of the term "coating" used herein include embodiments wherein a part or whole of the surface of the microparticle is coated. For this purpose, it is also effective that a pharmaceutically acceptable amount of a liquid water-soluble polymer and/or a surfactant is dispersed on the surface of the microparticles.

Specific examples of the preferable surfactant include, for example, nonionic surfactants such as sorbitan fatty acid esters (e.g. glycerine monostearate (self emulsifiers) etc.), propylene glycol fatty acid esters (e.g. propylene glycol monostearate etc.), polyoxyethylene glycerine fatty acid esters (e.g. POE (15) glycerine ester etc.), polyethylene glycol fatty acid esters (e.g. POE (10) monostearate. PEG distearate etc.), polyoxyethylene alkyl ethers (e.g. POE (21) lauryl ethers, POE (20) stearyl ether etc.), polyoxyethylene hydrogenated castor oil derivatives (e.g. POE (80) hydrogenated castor oil, HCO60 HCO50 (available from Nikko Chemicals) etc., polyoxyethylene sorbitol-yellow bee wax derivatives (e.g. POE (20) sorbitol-yellow bee wax etc.), polyoxyethylene lanolin alcohols (e.g. POE (20) lanolin alcohol etc.O, polyoxyethylene sorbitol fatty acid esters (e.g. POE (6) sorbitol hexastearate etc.) and polyoxyethylene polyoxypropylene glycol derivatives (Pluronics (Wyandotle Chemicals Corp.) such as pluronic F68 (polyoxyethylene (160) polyoxypropylene (30) glycol) etc.); anionic surfactants such as dodecylsulfuric acid alkali metal salts (e.g. sodium dodecylsulfate etc.), stearic acid alkali metal salts (e.g. sodium stearate etc.) and palmiatic acid alkali metal salts (e.g. sodium palmitate etc.). Examples of the liquid surfactants includes Tweens such as Tween 20 and Tween 80 (available from Astra powder Co., U.S.A.). These surfactants may be used singly or two or more kinds may be used in combination in an appropriate ratio.

Examples of the preferable water-soluble polymer include dextrins, dextran sulfates, chondroitin sulfate alkali metal salts (e.g. sodium chondroitin sulfate) and polyethylene glycols (e.g. polyethylene glycol 1,000 (PEG 1,000), PEG 1,500, PEG 4,000, PEG 6,000, PEG 20,000). These water-soluble polymers may be used singly or two or more kinds may be used in combination in appropriate ratio.

The means for coating microparticles with a water-soluble polymer and/or a surfactant is not limited. Example of the means include the method of adding a water-soluble polymer and/or a surfactant into the substance to be pulverized in the step of pulverizing either the solid preparation or the roughly ground solid preparation. In this method, the solid water-soluble polymer and/or the surfactant may be added to the pulverizing system together with the substance to be pulverized as a mixture thereof or separately from the substance. Whether liquid or solid, the water-soluble polymer and/or the surfactant may be supplied to the pulverizing system as a solution in an appropriate solvent. Composition prepared by drying a solution or suspension of the antiaggregation agent and the water-soluble polymer and/or the surfactant in an appropriate solvent (e.g. water, alcohols such as methanol or ethanol etc.) or these composites separated from the solution may be pulverized together with the subject to be pulverized for this purpose.

Coating or dispersing the water-soluble polymer and/or the surfactant on the surface of the microparticles may be conducted by mixing them with the resultant microparticles obtained by pulverizing the solid preparation. The manner of the mixing includes freeze-drying the suspension of the microparticles, which is obtained by pulverizing the solid preparation in a solution of a solution of a water-soluble polymer and/or a surfactant solutions in appropriate solvent (e.g. water, alcohols such as methanol or ethanol etc.). An appropriate amount of any antiaggregation agent may be added in the suspension. The antiaggregation agent may be any of ones described above. The preferable examples for the purpose of maintaining the shape after freeze-drying includes mannitol, D-sorbitol, glucose, sucrose, lactose, dextrine, dextran sulfate, chondroitin sulfate and like. The concentration of the water-soluble polymer and/or the surfactant in the solution used as dispersing solvent for microparticles, in the freeze-drying method, is in the range from about 0.000001% (w/v) to about 10% (w/v), preferably from about 0.0001% (w/v) to about 3% (w/v), more preferably about 0.001% (w/v) to about 0.5% (w/v). Further, addition of a buffering agent (e.g. phosphate buffer, citric buffer etc.), an osmotic pressure adjustor (e.g. sodium chloride, saccharides (e.g. mannitol, sorbitol, lactose) etc.) or the like is also effective to make more uniform the dispersion ability in the solvent for freeze-drying method.

Among the above-mentioned manners for coating, the method using the freeze-drying is preferable.

The content ratio of the water-soluble polymer and/or the surfactant relative to the microparticles to be coated is not limited as long as they can improve the dispersion ability of the microparticles. Specifically, the ratio is chosen from the range from about 0.0000001 to about 10-fold, preferably about 0.000005 to about 5-fold, more preferably about 0.00001 to about 0.01-fold by weight.

As the antiaggregation agent, use is generally made of a non-adhesive substance which is soluble in water, administerable to the human and is in a solid form at the ordinary temperature (about 15° C. to 25° C.). Specific examples include, for example, inorganic salts (e.g. the above described halogenated alkali metal salts, halogenated alkali earth metal salts, carbonate salts or bicarbonate salts with alkali metal, carbonate salts of alkali earth metal, phosphate salts with alkali metal, oxide of alkali earth metal, hydroxide of alkali earth metal etc.); alkali metal salts or alkali earth metal salts with acetic acid (e.g. sodium acetate, potassium acetate, magnesium acetate, calcium acetate etc.); organic acids (e.g. citric acid, tartric acid, malic acid, succinic acid, salicilic acid, chondroitin sulfuric acid, dextran sulfuric acid, carboxymethyl cellulose, arginic acid, pectic acid etc.) and salts thereof (e.g. alkali metal salts, alkali earth metal salts etc.); water-soluble saccharide (e.g. mannitol, sorbitol, lactose, glucose, sucrose, starchs (e.g. corn starch, potate starch) etc.); amino acids (e.g. glycine, phenylalanine, cysteine, arginine etc., preferably cysteine or arginine); proteins (e.g. gelatine, fibrine, coragen, albumin); water soluble cellulose (e.g. crystalline cellulose, carboxymethyl cellulose or salts thereof); and a like. These may be used in combination with one kind or two or more kinds in appropriate ratio. Among them, inorganic salts, water soluble saccharides and amino acids are preferable.

The amount of the antiaggregation agent to be used relative to the microparticle may not be limited as long as it has the effect of minimizing aggregation, and specifically selected from the range from about 0.001 to about 100-fold, preferably about 0.01 to about 50-fold, more preferably about 0.1 to about 10-fold by weight.

The thus-obtained microparticle can be administered as such or in the form of various dosage forms. It may be used as a starting material for producing such dosage forms. Examples of the dosage forms include injections (e.g., intramuscular, subcutaneous or visceral injections etc.), oral preparations (e.g., capsules, granules, powders, tablets etc.), external preparations (e.g., transnasal preparation, percutaneous preparations etc.) and suppositories (e.g., rectal suppository, vaginal suppository etc.).

The drug content in these dosage forms varies depending on the kind of the drug, dosage form, target disease etc. The contents may generally be chosen within the range from about 1 mg to about 200 mg, preferably about 3 mg to about 150 mg, more preferably about 5 mg to about 100 mg relative to the 1 g of the whole preparation.

These pharmaceutical preparations can be produced by a per se known method conventionally used in the pharmaceutical manufacturing field.

An injectable preparation can be prepared by, for example, suspending the microcapsules in an aqueous solvent such as water, if necessary, a dispersing agent (e.g., Tween 80, HCO-60, carboxymethyl cellulose (including carboxymethyl cellulose sodium), sodium alginate, etc.), a preservative (e.g., methyl paraben, propyl paraben, etc.), an isotonizing agent (e.g., sodium chloride, mannitol, sorbitol, glucose, etc.) etc. may be added, to yield an aqueous suspension, or by dispersing it in a vegetable oil such as olive oil, sesame oil, peanut oil, cotton seed oil or corn oil or propylen glycols, to yield an oily suspension, whereby a practically usable sustained-release preparation is obtained.

A preparation for oral administration can be prepared according to a per se known method, for example, mixing microparticles along with diluents (e.g. lactose, sucrose, starch etc.), disintegrators (e.g. starch, calcium bicarbonate etc.), binders (e.g. starch, arabia gum, carboxymethylcellulose, polyvinyl pyrrolidone, hydroxypropylcellulose etc.), lubricants (e.g. talc, magnesium stearate, polyethylene glycol.6,000 etc.) etc., and subjecting the mixture to compression molding or filling the mixture into a capsule, if necessary followed by subjecting the resultant product to a known coating method for purposes such as masking the taste, enteric coating and prolongation, to provide the oral dosage form. As the coating agent, film forming agents such as hydroxypropylmethylcellulose, ethylcellulose, hydroxymethylcellulose hydroxypropylcellulose polyoxyethylene glycol, Tween 80, Pluroric F68, cellulose acetate futalate, hydroxypropylmethylcellulose futalate, hydroxymethylcellulose acetate succinate and Eudragit (Rohm & Pharm Germany); methacrylic acid/ acrylic acid copolymer and coloring agents such as titanium oxid or iron sesquioxide are used.

As a external preparation, for example, a transnasal preparation in a form of solid, semi-solid or liquid can be prepared using the microparticles according to the per se known method. The microparticles can be used as such or mixed with diluents (e.g. glycol, mannitol, starch, microcrystalline cellulose etc.), thickeners (e.g. natural gums, cellulose derivatives, acrylic acid polymers etc.), etc., to provide the solid transnasal preparation in a form of powder composition. The liquid preparation can be prepared in a form of oily suspension or aqueous suspension by the same manner as the above-mentioned injectable preparation. The semi-solid preparation is preferably prepared in a form of an aqueous or oily gel or an ointment. Any of these preparations may comprise pH adjuster (e.g. carbonic acid, phosphonic acid, citric acid, hydrogen chloride, sodium hydroxide, etc.), antiseptics (e.g. p-hydroxybenzoate esters, chlorobutanol, benzalkonium chloride etc.) and the like.

In the case where microparticles are formulated into a suppository, an oily or aqueous suppository in a form of solid, semi-solid or liquid can be prepared from them in accordance with a per se known method. Oleaginous base used in these compositions may be any one as long as it cannot dissolve the microparticles, and examples of such oleaginous base includes higher fatty acid glycerides (e.g. cacao butter, Witepsols (Dinamitenovel Co.) etc.), middle chain fatty acids (e.g. MIGLYOLS (Dinamitenovel Co.) etc.) and vegetable oils (e.g. sesame oil, soybean oil, cotton seed oil etc.), aqueous base used therein includes polyethylene glycols and propylene glycols, for instance. Base for aqueous gel includes natural gums, cellulose derivatives, vinyl polymers and acrylic acid polymers, for instance.

The dosage of the microparticles produced in the present invention may be an effective amount of the active ingredients, i.e. the compound represented by the formula [I], although depending on type and content of the compound, duration of drug release and subject animals (e.g. mouse, rat, horse, cattle, human etc.) etc.

For example, when benzothiepine derivatives or a pharmaceutically acceptable salt thereof are administered to an adult subject in need (weighing 50 kg ) in a form of the microparticle produced in the present invention for treating a bone disease, its dosage can be selected from the range from about 0.35 mg to about 70 mg based on the active ingredient per administration.

When the microparticles are administered in the form of suspension injection, volume of injection may be chosen within the range from about 0.1 ml to about 5 ml, preferably about 0.5 ml to about 3 ml.

Since the particle size of the resultant microparticles can be well managed according to the production method of the present invention, there can be provided a sustained-release preparation having excellent pharmaceutical properties and well controlled drug release, as a useful medicament for preventing/treating bone diseases which need long dosage periods of administration, which comprises a compound represented by the formula [I], known to have a bone resorption suppressing activity, bone-metabolism-improving activity and osteogenesis-promoting activity.

BEST MODE FOR CARRYING OUT THE INVENTION

The present invention is hereinafter described in more detail by means of the following working examples, which are not to be construed as limitative.

EXAMPLE

Example 1

In 160 grams of dichloromethane were dissolved 10.0 g of (2R,4S)-(−)-N-[4-(diethoxyphosphorylmethyl)phenyl]-1,2,4,5-tetrahydro-4-methyl-7,8-methylenedioxy-5-oxo-3-benzothiepine-2-carboxamide (prepared according to Japanese Patent Laid Open Publication No. Hei8-231569 (hereinafter, referred to as "Compound A") and 90 grams of dl-lactic acid/glycolic acid copolymer (hereinafter referrd to as "copoly (dl-lactic/glycolic acid)") The lactic acid/glycolic acid ratio (hereinafter simply abbreviated as (L/G))=85/15; Weight-average molecular weight: 14,000. The resultant solution was poured into a container coated with fluorine-containing resin. The container was put in a vacuum drier to evaporate the solvent. The resultant solid dispersion was roughly ground and mixed with mannitol (15 g) and polyoxyethylene (160) polyoxypropylene (30) glycol (Pluronic F68) (2 g). The resultant mixture was powdered by a supersonic jet mill (PJM-100SP of NIPPON PNEUMATIC MFG CO. LTD.) under 0.3 MPa pressure of the compressed supplying gas. The resultant powder was kept in a vacuum drier at 45° C. under an inside pressure of 0.1 to 0.05 Torr for 3 days. Particles whose encapsulation rate of drug was at 100%, having an average particle diameter of 32 μm, having excellent dispersion ability in dispersion medium and gradually releasing the active ingredient for about 1 month in the muscle of rats were obtained.

Example 2

In dichloromethane (20 g) were dissolved Compound A (1.5 g) and copoly (lactic/glycolic acid) (L/G=90/10. Weight-average molecular weight: 14,000) (6.0 g). The resultant solution was poured into a stainless steel container, and the container was dried in a vacuum drier at 50° C. under an inner pressure of 10 to 0.01 Torr. The resultant dried substance was roughly ground, followed by addition of sodium chloride (1.5 g) and polyethyleneglycol 4000 (0.2 g) and mixing. The resultant mixture was pulverized in a turbocounter jet mill (TJ-0624 of Turbo Industry) under 0.2 MPa pressure of compressed supplying gas. There were obtained particles whose drug encapsulation rate is 100%, which have an average particle diameter of 27 μm and can gradually release the active ingredient for about 1 month in the muscle of rats.

Example 3

In dichloromethane (26.7 g) were dissolved Compound A (1.9 g) and copoly (lactic/glycolic acid) (L/G=85/15. Weight-average molecular weight: 14,900) (15.1 g). The resultant solution was poured into a container coated with fluorine-contained resin. The container was put in a vacuum drier to evaporate the solvent. The resultant solid dispersion was roughly ground, followed by addition of mannitol (3 g). The resultant mixture was pulverized by a supersonic jet mill (PJM-100SP of NIPPON PNEUMATIC MFG CO. LTD.) under 0.1 MPa pressure of compressed supplying gas. The resultant powder was dispersed in an aqueous amino acid solution (containing arginine acid 3.8% or cysteine 2.7%), followed by being freeze-dried to provide particles. One hundred mg of the particles were filled into a 9P vial and subjected to a stability test at 40° C. 75% RH for 4 months, and found to be stable without causing any agglomeration between particles.

Example 4

In dichloromethane (300 g) are dissolved the Compound A (10 g) and copoly (dl-lactic/glycolic acid) (L/G=90/10. Weight-average molecular weight: 13,000) (90 g). The resultant solution is poured into a container coated with fluorine-contained resin, and the container is dried in a vacuum drier at 50° C. under an inner pressure not higher than 10 Torr. The dried substance thus obtained is roughly ground, followed by addition of sodium citrate (20 g) and the polyethylene glycol 4000 (2 g) and mixing. The mixture is sieved to collect the particles which pass through the sieve of 2 mm mesh. The resultant particles are pulverized by a supersonic jet mill (PJM 100sp of NIPPON PNEUMATIC MFG CO. LTD.) under 0.3 MPa pressure of compressed supplying gas.

Example 5

In dichloromethane (300 g) a re dissolved Compound A (10 g) and copoly (dl-lactic/glycolic acid) (L/G=80/20. Weight-average molecular weight: 15,000) (90 g). The resultant solution is poured into a container coated with fluorine-contained resin. The container is dried in a vacuum drier at 50° C. under the inner pressure not higher than 10 Torr to dry the solution. The dried substance is roughly ground, followed by addition of mannitol (20 g). The mixture is sieved to collect the particles which pass through the sieve of 2 mm mesh. The resultant particles are pulverized by a supersonic jet mill (PJM-100SP of NIPPON PNEUMATIC MFG CO. LTD.) under 0.2 MPa pressure of compressed supplying gas.

Industrial Applicability

According to the production method of the present invention, there can be produced efficiently and on a large scale, a sustained-release preparation having excellent pharmaceutical properties and well-controlled drug-release. The microparticles produced by the method of the present invention is useful as a medicament for preventing/treating bone diseases which need long dosage period of administration, which comprises a compound represented by the formula [I], known to have a bone resorption suppressing activity, bone-metabolism-improving activity and osteogenesis-promoting activity.

We claim:

1. A method for producing a microparticle which comprises pulverizing a solid preparation comprising a compound represented by the formula:

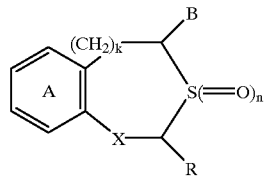

wherein ring A is an optionally substituted benzene ring; R is a hydrogen atom or an optionally substituted hydrocarbon group; B is an optionally esterified or amidated carboxyl group; X is —CH(OH)— or —CO—; k is 0 or 1; and n is 0, 1 or 2, or a pharmaceutically acceptable salt thereof and a biodegradable polymer of α-hydroxycarboxylic acid in the presence of a pulverizing auxiliary.

2. A method according to claim 1, wherein the compound is a compound represented by the formula:

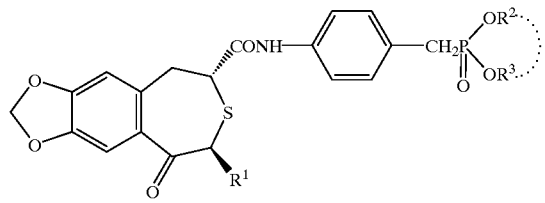

wherein $R^1$ is a hydrogen atom or an optionally substituted hydrocarbon group; and $R^2$ and $R^3$ are independently a lower alkyl group or bind together to form a lower alkylene group.

3. A method according to claim 2, wherein $R^1$ is a methyl group, and $R^2$ and $R^3$ are ethyl group.

4. A method according to claim 1, wherein the weight-average molecular weight of the polymer of the α-hydroxycarboxylic acid is about 3,000 to about 30,000.

5. A method according to claim 1, wherein the α-hydroxycarboxylic acid is lactic acid and/or glycolic acid.

6. A method according to claim 1, wherein the solid preparation is a solid dispersion.

7. A method according to claim 1, wherein the pulverizing auxiliary is a sugar or a sugar alcohol.

8. A method according to claim 1, wherein the pulverizing auxiliary is an organic acid, a salt thereof or a salt of an inorganic acid.

9. A method according to claim 1, wherein the solid preparation is pulverized with a water-soluble polymer and/or a surfactant.

10. A method according to claim 1, which further comprises a step for coating the microparticle with a water-soluble polymer and/or a surfactant.

11. A method according to claim 9 or 10, wherein the water-soluble polymer is a polyethylene glycol.

12. A method according to claim 11, wherein the polyethylene glycol is polyethylene glycol 4000.

13. A method according to claim 9 or 10, wherein the surfactant is a nonionic surfactant.

14. A method according to claim 13, wherein the surfactant is polyoxyethylene (160) polyoxypropylene (30) glycol.

15. A microparticle produced by pulverizing a solid preparation comprising a compound represented by the formula:

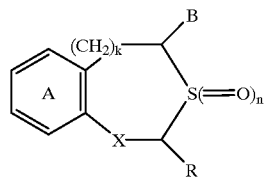

wherein ring A is an optionally substituted benzene ring; R is a hydrogen atom or an optionally substituted hydrocarbon group; B is an optionally esterified or amidated carboxyl group; X is —CH(OH)— or —CO—; k is 0 or 1; and n is 0, 1 or 2, or a pharmaceutically acceptable salt thereof and a biodegradable polymer of α-hydroxycarboxylic acid in the presence of a pulverizing auxiliary.

* * * * *